United States Patent [19]

Tanabe et al.

[11] Patent Number: 5,116,830
[45] Date of Patent: May 26, 1992

[54] STEREOISOMERICALLY PURE 17α-ETHYNYL-ESTRA-2-EN-17β-OL AND THE 17β ESTERS THEREOF, METHODS OF PREPARATION AND USES

[75] Inventors: Masato Tanabe, Palo Alto; David F. Crowe, Yreka; Richard H. Peters, San Jose; John G. Johansson, Menlo Park, all of Calif.

[73] Assignee: SRI International, Menlo Park, Calif.

[21] Appl. No.: 873,074

[22] Filed: Jun. 2, 1986

Related U.S. Application Data

[63] Continuation of Ser. No. 641,750, Aug. 17, 1984, abandoned.

[51] Int. Cl.[5] .......................... A61K 31/58; C07J 5/00; C07J 7/00; C07J 1/00
[52] U.S. Cl. .................. 514/182; 552/557; 552/599; 552/602; 552/610; 552/650; 552/645; 552/505; 552/506; 540/5
[58] Field of Search .................... 260/397.5; 514/182; 552/557, 645, 650, 610, 599, 602

[56] References Cited

U.S. PATENT DOCUMENTS

| | | | |
|---|---|---|---|
| 3,624,203 | 11/1971 | Overbeek | 424/238 |
| 3,875,188 | 4/1975 | Galantay | 260/397 |
| 4,278,668 | 7/1981 | Gueritee | 260/397.5 |

FOREIGN PATENT DOCUMENTS

| | | |
|---|---|---|
| 057115 | 8/1982 | European Pat. Off. . |
| 0066001 | 12/1982 | European Pat. Off. . |
| 919565 | 2/1963 | United Kingdom . |
| 961502 | 6/1964 | United Kingdom . |
| 1492746 | 11/1977 | United Kingdom . |

OTHER PUBLICATIONS

Bowers et al. J. Organic Chemistry vol. 63 (1963) pp. 156–161.
"Steroids CCV[1], Ring a modified hormone analogs. Part I, some Ring a olefins," A. Bowers et al., J. Medicinal Chem. vol. 6, No. 2, Mar. 6, 1963, Washington, D.C.
"A new synthesis of Δ steroids", Marcel Fetizon, J. Chem. Soc., Chem. Comm. vol. 3, 1969, p. 112.
"Reductive cleavage of vinyl phosphates: preparation of 17β-tert-butoxy-5α androst-2-ene," Org. Syn. vol. 61, 1983, pp. 116–119.
R. Villotti et al., "Optical Rotatory Dispersion Studies. XXXVII. Steroids. CXLVI. On the Mechanism and Stereochemical Course of the Bromination of 3-Keto Steroids and Their Erol Acetates," *Journal of the American Chemical Society*, vol. 82, pp. 5693–5700 (1960).
J. R. Reel, et al., "Competitive Progesterone Antagonists: Receptor Binding and Biologic Activity of Testosterone and 19-Nortestosterone Derivatives", *Fertility and Sterility*, vol. 31, No. 5, pp. 522–561 (1959).
M. K. McPhail, "The Assay of Progestin", *J. Physiology* (London), vol. 83, pp. 146 ff (1935).
C. Djerassi, "Steroid Oral Contraceptives", *Science*, vol. 151, pp. 1051–1061 (Mar. 4, 1966).
J. Fried and J. Edwards, *Organic Reactions in Steroid Chemistry*, vols. I and II, von Nostrand Reinhold Co., New York, NY (1973).
C. Djerassi (ed.) *Steroid Reactions: An Outline For The Organic Chemist*, Holden-Day Publishing Co., Inc., Belmont, Calif., 1964.

Primary Examiner—Frederick E. Waddell
Assistant Examiner—T. J. Criares
Attorney, Agent, or Firm—Richard P. Lange

[57] ABSTRACT

This invention relates to a stereoisomerically pure $\Delta^2$ compound of the formula (I):

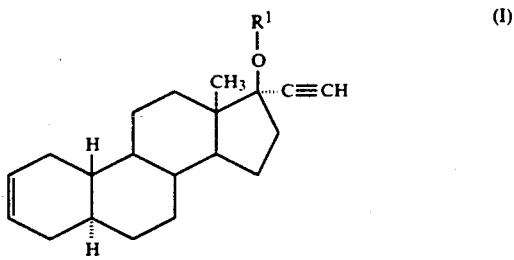

(I)

wherein:
$R^1$ is hydrogen or $-(C=O)-R^2$, wherein:
$R^2$ is an organic substituent selected from the group consisting of alkyls, alkenyls, alkynyls, cycloalkyls, cycloalkylalkylenes, haloalkyls, aryls, haloaryls and arylalkylenes, and their product by the process of:
(a) reacting the 17β-hydroxy group of 17β-hydroxy-5α-estr-1-en-3-one with dihydropyran to produce the 3-keto-17β-ether;
(b) reducing the 3-keto-17β-ether product of step (a) with lithium in ammonia;
(c) reacting the product of step (b) with dialkyl chlorophosphate to produce the 3-substituted phosphate;
(d) reducing the product of step (c) with lithium and ammonia to produce the $\Delta^2$-protected-17β-ether product;
(e) hydrolysis of the produce of step (d) to product the $\Delta^2$-17β-hydroxy compound;
(f) oxidizing the 17β-hydroxy product of step (e) to produce the 17-keto compound;
(g) reacting the 17-keto derivative of step (f) with acetylene magnesium halide to produce the compound of formula I where $R^1$ is hydrogen; and
(h) optionally reacting the product of step (g) with an acyl halide or acyl anhydride to produce the compound of formula I wherein $R^1$ is acyl. The invention also relates to a pharmaceutical composition for oral administration comprising a compound of formula I and to a method of achieving contraception (fertility-control) in a female mammal. The compound of formula I has antiprogestational activity in a female mammal and is useful in the control of fertility, having substantially no undesirable side effects.

25 Claims, No Drawings

5,116,830

1

STEREOISOMERICALLY PURE 17α-ETHYNYL-ESTRA-2-EN-17β-OL AND THE 17β ESTERS THEREOF, METHODS OF PREPARATION AND USES

The invention described herein was made in the course of work under a contract from the U.S. National Institutes of Health No. NOl-HD-2809 of the Department of Health and Human Resources.

This application is a continuation of application Ser. No. 641,750, filed Aug. 17, 1984, and now abandoned.

BACKGROUND OF THE INVENTION

1. Field of the Invention

The present invention is in the field of steroid chemistry. More particularly, it concerns the stereoisomerically pure 17α-ethynyl-estra-2-en-17β-ol, its 17β-hydroxy esters, and their preparation and use in the control of female fertility in mammals, particularly female human beings. These compounds have antiprogestational activity.

2. Related Art

The use of substituted steroids for the control of conception in female mammals has been known for some time, see for example, G. Pincus et al. in Science, Vol. 124, p. 890 (1956); J. Rock et al. in Science, Vol. 124, p. 891 ff (1956); G. Pincus, The Control of Fertility, Academic Press, New York, New York, published in 1965; and C. Djerassi, Science, Vol. 151, p. 3716 (1966).

17α-Ethynyl-estra-2-en-17β-ol is a known compound See, A. Bowers et al., in Steroids, Vol. 6, pp. 156 to 161 (1963). In practice as shown herein, the synthetic route described by Bowers et al. produces a mixture of 17β-hydroxy compounds, i.e. the $\Delta^2$ and $\Delta^3$ isomers. A pure isomer is not produced. Further, no biological data is presented for the effect of this compound in a mammalian system. Bowers et al. show that these products have androgenic effects, but the reference does not disclose their use for fertility control in females.

In U.S. Pat. No. 3,624,203, Overbeek discloses compounds of the formula:

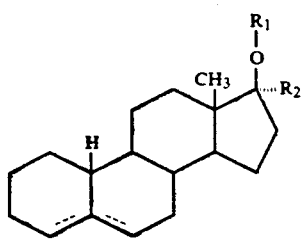

in which

R₁ is H or an acyl group or an alkyl group;

R₂ is an alkyne group of two to four carbon atoms; and in which there is one ethylenic bond connecting carbon atom five with carbon atom four or carbon atom six.

The series of compounds described by Overbeek are useful as oral contraceptives for females. These steroid structures are different from the ones described herein. In other words, all of compounds described by Overbeek have either a carbon-carbon double bond at C(4)-C(5) or C(5) to C(6), rather than at C(2) to C(3) as in the compounds of the present invention.

2

In U.S. Pat. No. 4,278,668, Guéritée discloses compounds of the formula:

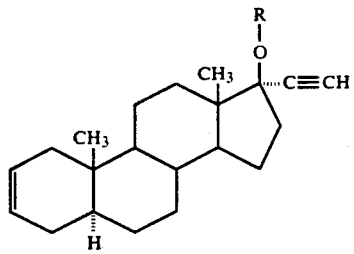

in which R is hydrogen or an acetyl group. These compounds are effective in the treatment of endometriosis (the presence of uterus mucous membrane lining tissue in abnormal locations, including the uterine wall, ovaries, or extragenital sites). The Guéritée compounds possess a 19-methyl group whereas the compounds of interest described herein do not have a 19-methyl group (i.e. the 19-nor-derivative).

In U.S. Pat. No. 3,875,188, Galantay disclosed 17α-(lower alkyl) allenyl steroids of the general formula:

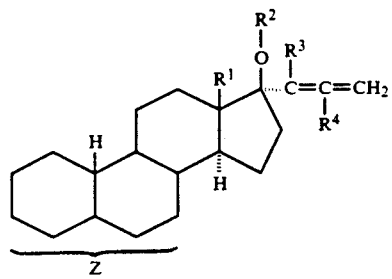

wherein:

R¹ is alkyl of 1 to 3 carbon atoms;

R² is hydrogen, or lower alkanoyl having 2 to 4 carbon atoms;

R³ is alkyl having 1 to 3 carbon atoms;

R⁴ is hydrogen, hydroxy or lower alkynoyloxy; and

Z embracing rings A and B has a number of substituents. These compounds are useful as fertility control agents in animals. However, none of these allenyl steroids are disclosed in the present invention.

In British Patent No. 919,565, is disclosed the preparation of 17α-chloroethynyl steroid derivatives which have hormonal properties, including oestrogenic, progestational, ovulation-inhibiting and claudogenic antifertility properties. Unsaturated derivatives including a $\Delta^2$-isomer are disclosed. However, no disclosure is made concerning the 17α-ethynyl-17β-hydroxy steroids or the 17β-acyloxy compounds of the present invention.

British Patent No. 961,502 discloses a number of 17α-butadynyl-17β-hydroxy steroids. The compounds have useful oestrogenic and claudogenic properties. However, none of the compounds or intermediates disclosed is 17α-ethynyl-estra-2-en-17β-ol or its 17β-esters.

The present invention concerns a group of steroid compounds having antiprogestational activity which are useful in the control of fertility in female mammals.

SUMMARY OF THE INVENTION

In one aspect this invention concerns the stereoisomerically pure 17α-ethynyl-estra-2-en-17β-ol and the 17β-esters thereof. These materials are represented structurally by the general formula (I):

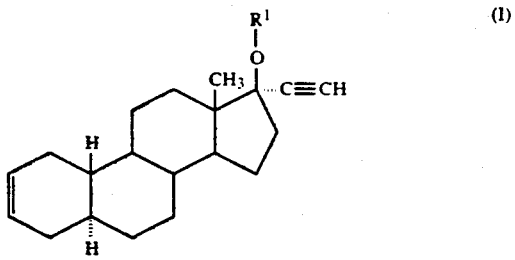

where

R$^1$ is hydrogen in the case of the 17 β-ol compound or an acyl substituent in the case of the 17 β-esters. The acyl substituent has the formula:

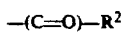

wherein

R$^2$ is an organic substituent selected from the group consisting of alkyls, alkenyls, alkynyls, cycloalkyls, cycloalkylenes, haloalkyls, aryls, haloaryls and arylalkylenes.

These compounds are produced by a stereospecific process. This process employs a lithium in ammonia reduction of a 3-substituted phosphate steroid derivative to specifically produce a Δ$^2$-structure (i.e. unsaturated). This stereospecific reduction is an aspect of this invention as are the 3-substituted phosphates of the formula:

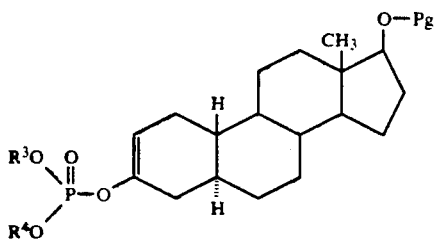

wherein:

R$^3$ and R$^4$ are each independently lower alkyl groups having 1 to 6 carbon atoms; and Pg is an oxygen protecting group.

The stereospecific reduction step can find application in the overall process to produce the compounds of this invention, which process comprises:

(a) reacting the 17β-hydroxy group of 17β-hydroxy-5α-estr-1-en-3-one with a protecting group, Pg, such as dihydropyran, to produce the 3-keto compound having a protected 17β-hydroxy group;

(b) reducing the 3-keto product of step (a) with lithium in ammonia;

(c) reacting the product of step (b) with dialkyl chlorophosphate to produce the 3-substituted phosphate;

(d) reducing the product of step (c) with lithium and ammonia to stereospecifically produce the Δ$^2$-17β-protected product;

(e) hydrolyzing of the product of step (d) to produce the Δ$^2$-17β-hydroxy compound;

(f) oxidizing the 17β-hydroxy product of step (e) to produce the 17-keto compound;

(g) reacting the 17-keto derivative of step (f) with acetylene magnesium halide to produce the compound of formula I wherein R$^1$ is hydrogen; and (h) optionally reacting the product of step (g) with an acyl halide or acyl anhydride to produce the compounds of formula I wherein R$^1$ is acyl.

This invention produces compounds which are substantially pure Δ$^2$-isomers, and not a mixture of the Δ$^2$ and Δ$^3$-isomers.

These compounds are usually administered orally and are useful in the control of female mammalian fertility. These compounds have antiprogestational activity, with a minimum of undesirable side effects. The pharmaceutical compositions, and uses of these compounds to control fertility constitute additional aspects of this invention.

DETAILED DESCRIPTION OF THE INVENTION

The stereoisomerically pure Δ$^2$-compounds of this invention are defined by the general formula I wherein R$^1$ is hydrogen or an acyl substituent of the formula, —(C=O)—R$^2$, wherein R$_2$ is an alkyl, alkenyl, alkynyl, cycloalkyl, cycloalkylalkylene, haloalkyl, aryl, haloaryl, or arylalkylene group.

As used herein

"Acyl" refers to a group of the structure —(C=O)—R$^2$, where R$^2$ is as described herein. Acyl, therefore, includes such groups as, for example, acetyl, propanoyl (or propionyl), isopropanoyl, n-butanoyl (or n-butyryl), octanoyl, eicosanoyl, propenoyl (or acryloyl), 2-methylpropenoyl (or methacryloyl), octanoyl, tetradecenoyl, eicosenoyl, tetracosenoyl, propynoyl, 2-butynoyl, n-2-octynoyl, n-2-tetradecynoyl, 2-chloropentanoyl, 2-chlorotetracosanyl, 3-bromo-2-methacryloyl, benzoyl, 1- and 2-naphthoyl, phenylacetyl, 6-phenylhexylenoyl, and the like.

"Alkenyl" refers to a branched or unbranched unsaturated hydrocarbon group of 2 to 24 carbon atoms and one or more unsaturated carbon-carbon bonds, such as for example, ethenyl, 1-propenyl, 2-propenyl, 1-butenyl, 2-isobutenyl, octenyl, decenyl, tetradecenyl, Δ$^{8,11}$-heptadecadienyl, hexadecenyl, eicosenyl, tetracosenyl and the like.

"Alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like.

"Alkylene" refers to a difunctional saturated branched or unbranched hydrocarbon chain containing from 1 to 6 carbon atoms, and includes, for example, methylene (—CH$_2$—), ethylene (—CH$_2$—CH$_2$—), propylene (—CH$_2$—CH$_2$—CH$_2$—), 2-methylpropylene [—CH$_2$—CH(CH$_3$)—CH$_2$—], hexylene [—(CH$_2$)$_6$—] and the like.

"Alkynyl" refers to a branched or unbranched acetylenically unsaturated hydrocarbon group of 2 to 24 carbon atoms such as ethynyl, 1-propynyl, 2-propynyl, 1-butynyl, 2-butynyl, octynyl, decynyl, tetradecenyl, hexadecynyl, eicosynyl, tetracosynyl and the like.

"Aryl" refers to a phenyl or 1- or 2-naphthyl group. Optionally, these groups are substituted with one to four lower alkyl groups (having from one to six carbon atoms).

"Arylalkylene" refers to an aryl group as is defined herein which is attached to one end of an alkylene group as is defined herein. As used herein, the other end of the alkylene group is attached to the carbon of the carbonyl group to form the acyl group.

"Cycloalkyl" refers to a saturated hydrocarbon ring group having from 3 to 8 carbon atoms, and includes, for example, cyclopropyl, cyclobutyl, cyclohexyl, methylcyclohexyl, cyclooctyl, and the like.

"Cycloalkylalkylene" refers to a saturated hydrocarbon containing a cycloalkyl group as is defined herein and an alkylene group as is defined herein. The term includes, for example, cyclopropylmethylene, cyclobutylethylene, 3-cyclohexyl-2-methylpropylene, 6-cyclooctylhexylene, and the like.

"Halo" or "halogen" refers to fluoro, chloro, bromo or iodo, usually regarding halo substitution for a hydrogen atom in an organic compound.

"Haloalkyl" refers to an "alkyl" group in which one to four, especially one of its hydrogen atoms, is substituted by a "halogen" group.

"Haloaryl" refers to an "aryl" group substituted with from one to four halogen groups.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

The compounds of the present invention are generally named according to the IUPAC or Chemical Abstracts Service nomenclature, system. The substituents on the ring system are as depicted above in the Summary of the Invention. For example, when the group attached at the 17-carbon atom of the steroid is acyloxy, i.e. —O—(C=O)—R$^2$, and R$^2$ is ethyl, the compound of formula I is named 17α-ethynyl-estra-2-en-17β-ol propionate or 17α-ethynyl-17β-propionyloxy-estra-2-ene, and is shown below:

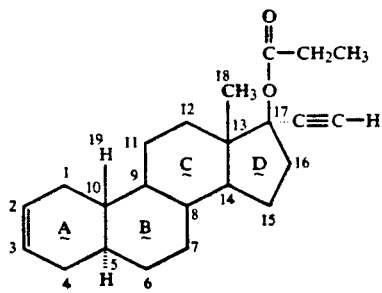

The five or six membered rings of the steroid molecule are often designated A, B, C and D as is shown immediately above.

Preferred compounds of the present invention are the 17-ol, and those ester compounds of formula I wherein R$^2$ is an alkyl, or an aryl. A more preferred subgroup includes the 17β-ol and those ester compounds of formula I wherein R$^2$ is a normal (i.e., straight chain) alkyl, of from 1 to 16 carbon atoms. Especially preferred compounds are those esters where R$^2$ is ethyl, n-hexyl, n-nonyl, n-tridecyl, phenyl or 2-phenylethylene.

The compounds of the present invention are stereoisomerically pure. That is, they are not mixtures of two or more stereoisomers—rather they consist essentially of pure Δ$^2$ materials—with other isomers present in only minor amounts, preferably less than 1%.

Process for Preparation

Reaction Sequence 1 shown below may be used to prepare compounds of formula I. (Formula I is also subdivided into the compounds of formula Ia where R$^1$ is hydrogen, and formula Ib where R$^1$ is acyl of the formula —(C=O)—R$^2$, and R$^2$ is as defined herein.)

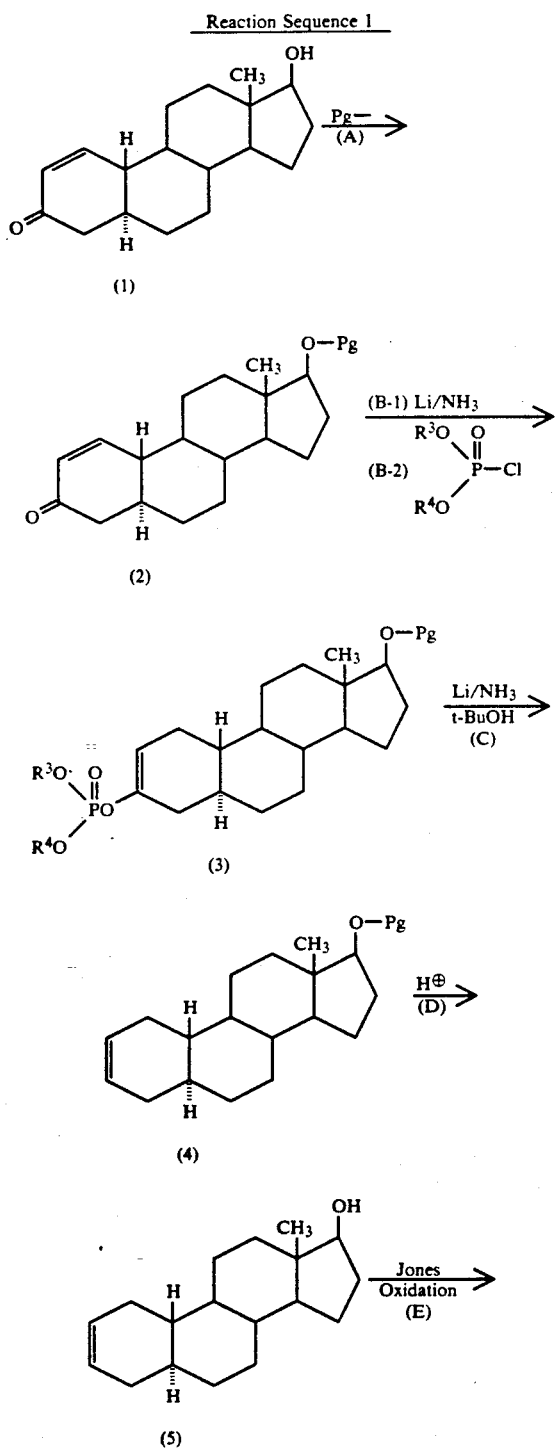

-continued
Reaction Sequence 1

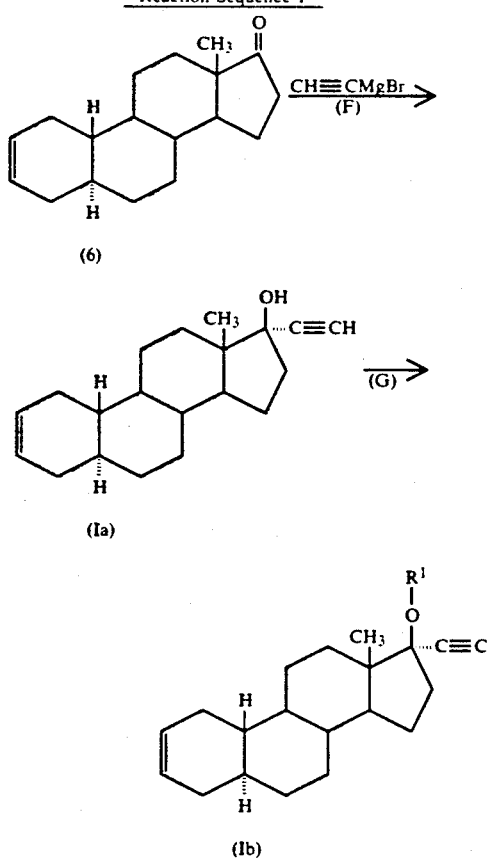

(6)

(Ia)

(Ib)

Reaction Sequence 1

The compounds of formula I (Ia and Ib) are prepared according to Reaction Sequence 1, Steps A to G, starting with 17β-hydroxy-5α-estr-1-en-3-one, Compound 1, which is prepared according to the method described by R. Villotti, et al., *J. Amer. Chem. Soc.*, Vol. 82, pp. 5693–5700 (1960), which is incorporated herein by reference.

Compound 2, 17β-protected oxygen-5α-estr-1-en-3-one, is obtained, according to Step A, by treating Compound 1 with a protecting group, Pg, for example, dihydropyran, in a non-protonated solvent, such as dichloromethane, diethyl ether, acetone or the like in the presence of a catalytic amount of strong acid, such as p-toluenesulfonic acid. The reagents are combined and stirred at about −10° to +25° C., preferably about 0° C., for about 0.5 to 10 hr, preferably about 3 hr. Alternative protecting groups such as t-butyldimethylsilyl or β-methoxymethylethers may also be used if desired. After purification, for instance, treatment with sodium bicarbonate, ether, and filtration through Florisil®, Compound 2 is recovered by removal of the solvent and chromatography using Florisil® with elution using a solvent mixture of ethyl acetate/hexane (33/66).

Compound 3, 17β-protected oxygen-3-dialkylphosphato-5α-estr-2-ene is obtained according to Steps B-1 and B-2. Compound 2 is first reacted with a strong reducing agent such as lithium in liquid ammonia in an inert nonprotonated solvent at low temperatures, of the order of about −78° C. for about 0.5 to 10 hr, perferably about 3 hr. The solvent is removed under vacuum.

The residue is treated without purification in Step B-2 with solvent and base, such as N,N,N',N'-tetramethylethylenediamine, and reacted with a phosphorylating agent, such as diethylchlorophosphate, at ambient temperature for about 1 to 24 hr, preferably about 16 hr. A precipitate forms within a short time after mixing the reagents. The solvent is removed under vacuum, and the residue is partitioned between water and ether. The ether phase is separated, and the aqueous phase is extracted with ether. The combined ether extracts are washed with water, brine and dried to produce an oil which is used in the subsequent step without purification. The dialkylphosphonate may be, for example, 17β-tetrahydropyranyloxy-3-diethylphosphato-5α-2-ene.

Compound 4, 17β-protected-5α-estr-2-ene, is obtained according to Step C, by treating Compound 3 with a strong reducing agent, such as lithium in ammonia, between −78° and 0° C., preferably about −40° C., for about 0.5 to 10 hr, preferably about 2 hr. Excess lithium is removed using an alcohol mixture, such as t-butanol/ethanol. After removal of the excess ammonia by evaporation, solvent is removed under reduced pressure. The solid residue is partitioned between water and a solvent, such as ether, and the aqueous phase is reextracted with ether. The combined solvent extracts are washed with water, brine and dried. Compound 4 is obtained after removal of the solvent and chromatography using Florisil®.

Compound 5, 17β-hydroxy-5α-estr-2-ene, is obtained according to Step D, by treatment of Compound 4 with a strong acid, such as aqueous hydrochloric acid (1N) in the presence of an alcohol, such as methanol, at ambient temperature for about 0.5 to 12 hr, preferably about 6 hr. The solvent is evaporated and the residue is dissolved in a water/ether mixture. The water phase is extracted with additional ether. The combined ether phases are washed with water, brine and dried. Compound 5 is obtained by evaporation of the solvent.

Compound 6, 5α-estr-2-en-17-one, is obtained according to Step E by dissolving Compound 5 in a solvent such as acetone. After cooling to −10° to +25° C., preferably about 0° to 5° C. is added dropwise an oxidizing reagent, such as Jones reagent, CrO₃/acetone, with stirring for less than an hour, preferably about 2-5 minutes. The excess oxidizing reagent is destroyed by treatment with an alcohol, such as isopropanol, and the solvent is removed in vacuum. The solid product is partitioned between water/ether, and the water phase is extracted with additional solvent. The combined solvent phase is washed with water, brine, and dried. Evaporation of the solvent produces Compound 6.

Compound Ia, 17β-hydroxy-17α-ethynyl-5α-estr-2-ene, is obtained, according to Step G by reaction of a solution of Compound 6 with an ether solution of acetylene magnesium halide (bromide) at about −10° to +25° C., preferably 0° C., for about 0.5 to 6 hr, preferably about 2 hr. The reaction mixture is then stirred at ambient temperature for about 1 to 24 hr, preferably 16 hr. The reaction mixture is subsequently hydrolyzed, using preferably an ammonium chloride solution, followed by treatment with water and ether. The organic phase is separated and washed, dried and evaporated to dryness. Purification using column chromatography, preferably using silica gel and a mixture of ethyl acetate/hexane (50/50, v/v) as eluent produces Compound Ia.

Compounds of formula I, where $R^1$ is —(C=O)—$R^2$, and $R^2$ is as described herein (Compounds Ib), are prepared according to Step G by reacting the compound of formula I, where $R^1$ is H (Compound Ia), with an acyl anhydride, e.g., $R^2$—(C=O)—O—(C=O)—$R^2$ or mixed acyl anhydrides corresponding to the desired $R^2$, in the presence of an organic base, such as pyridine, at about ambient temperature for about 0.5 to 24 hr. Mixed anhydrides may include, $R^2$—(C=O)—O—(C=O)—$CF_3$, a mixture of two different anhydrides, $R^2$—(C=O)—O—(C=O)—$R^2$, and mixtures of anhydrides, including $CF_3$—(C=O)—O—(C=O)—$CF_3$. After neutralization and purification by procedures known in the art, the compound of formula I where $R^1$ is —(C=O)—$R^2$ (i.e., Ib) is obtained in good yield.

Alternatively, an acyl halide $R^2$—(C=O)—X, where X is halogen may be reacted with the compound of formula I wherein $R^1$ is H, in the presence of base under substantially the same conditions as is described immediately above for the anhydride.

In summary, then the compounds of formula I (Ia and Ib) are prepared by:

(a) reacting the 17α-hydroxy group of 17α-hydroxy-5α-estr-1-en-3-one with dihydropyran to produce the 3-keto-17α-ether;

(b) reducing the 3-keto-17β-ether product of step (a) with lithium in ammonia;

(c) reacting the product of step (b) with dialkylchlorophosphate to produce the 3-substituted phosphate;

(d) reducing the product of step (c) with lithium and ammonia to produce the $\Delta^2$-protected-17β-ether product;

(e) hydrolysis of the product of step (d) to produce the $\Delta^2$-17β-hydroxy compound;

(f) oxidizing the 17β-hydroxy product of step (e) to produce the 17-keto compound;

(g) reacting the 17-keto derivative of step (f) with acetylene magnesium halide to produce the compound of formula I.

To produce the 17β-acyloxy derivatives (Compound Ib) of the compounds of formula I, in step (h) the 17β-hydroxy product (Ia) of step (g) above is reacted with acyl halide or acyl anhydride to produce the compound of formula I where $R^1$ is —(C=O)—$R^2$, and $R^2$ is acyl as defined herein, (i.e., Ib).

Use of the Compounds

Another embodiment of the present invention involves a method useful in the control of female fertility in a mammal, particularly a human being, which method comprises administering to a subject in need of such treatment a fertility-controlling effective amount of the compound of formula I, particularly where $R^1$ is hydrogen (Ia). A preferred method includes oral administration of the compound of formula I, particularly where $R^1$ is —(C=O)—$R^2$ and $R^2$ is ethyl.

A preferred composition includes compositions comprising compounds of formula I for oral administration to a female human being, particularly where $R^1$ is hydroxyl, and also where $R^1$ is acyl and $R^2$ is ethyl.

Utility and Administration

The compounds of this invention have been shown to be effective in animal models for antiprogestin effect and, in the control of fertility in female mammals.

For instance, the compound of formula I where $R^1$ is hydrogen, when tested in rats, was found to have about 2.5 times the activity of a known antiprogestin, 17β-hydroxy-11β-(4-dimethylaminophenyl)-17α-(prop-1-ynyl)-estra-4,9-dien-3-one (S-1) in counteracting the effect on the uterus of 8 mg of progesterone administration to rabbits. (See Table 1).

TABLE 1

| Biological Testing Compounds Having Anti-Progestational Activity | | | |
|---|---|---|---|
| | | Dose Response (mg/kg) | Inhibition of Uterine Proliferation |
| S-1 | Standard EPO Patent No. 0057115 Compound RU-38486 | 80 | 1 |
| S-2 | Mixture $\Delta^2$- & $\Delta^3$-isomers (~90/10) (Bowers et al) | 26.9 | ~2.5 |
| S-3 | Pure $\Delta^2$-Isomer (>99%) (Claim 1) | ~16-20 | ~4.0-5.0 |

The biological testing is performed in the following manner. Six rabbits for each test, each weighing about 1000 to 1100 g, are orally administered each day with 0.2 mg of progesterone. At the same time each animal is orally administered with a one-fifth of amount per day of the compounds "S-1", "S-2", and "S-3" shown in Table 1. The standard compound S-1, which is the best antiprogestin compound yet tested requires a total of 80 mg/kg over 5 days to achieve 100% inhibition of uterine proliferation. Compound S-2, the mixture of $\Delta^2$- and $\Delta^3$-isomers described herein requires a total of 26.9 mg/kg over five days to obtain the desired degree of 100% inhibition of uterine proliferation. Compound S-3, the pure $\Delta^2$-isomer described herein requires about 16-20 mg/kg to obtain 100% inhibition of uterine proliferation. The effectiveness is obtained for compound S-1 by the ratio 80/80 as a standard. For mixture S-2 the effectiveness is 80/26.9 ~2.5, and for pure S-3 the effectiveness is 80/16-20 ~4.0-5.0. Thus, the pure $\Delta^2$-isomer is more effective in inhibition of uterine proliferation than the known compound and more effective than the $\Delta^2$-, $\Delta^3$-isomer mixtures. It is understood that under these circumstances that about 100% inhibition of uterine proliferation is essentially equivalent to about 100% control of fertility.

Alternatively, progestational and antiprogestational activity is assessed by the McPhail Modification of the Clauberg assay. Immature New Zealand White Rabbits (0.8 to 1.1 kg) receive subcutaneously injections of 5 g of estrone in peanut oil on days 1, 3, and 5. Progesterone and/or test compond or the peanut oil vehicle then are administered subcutaneously on days 7, 8, 9, and 10. On day 11 the rabbits are asphyxiated with carbon dioxide and the uteri are excised, weighed, and fixed in 10% formalin. The fixed tissues are embedded in paraffin, sectioned at 6 m, and stained with hematoxylin and eosin. Endometrial profileration are scored from 0 (estrone-primed controls to 4 (maximal proliferation) according to the grading system of McPhail. (See M. K. McPhail, *J. Physiol.* (London), Vol. 83, pp 146 ff (1963) and J. R. Reel, et al., *Fertility and Sterility*, Vol. 31, No. 5, pp 522–561 (1959), both of which are incorporated herein by reference.) Both biological assay methods produce essentially the same results.

Although not completely understood at this time, the compounds of this invention exhibit potent antiprogestin properties when orally administered. These compounds appear to have antiprogestional activity which interferes with progesterone utilization by the uterus and at the same time, do not have undesirable side effects. (G. Teutsch, et al., EPO Patent No. 0057115, and Abstr. 64th Ann. Endro Soc. Mtg. #668, P. 246 (1982).

Administration of the active compounds described herein can be via any of the accepted modes of administration for therapeutic agents. These methods include oral, rectal, parenteral, transdermal, subcutaneous and other system modes. The preferred method of administration is oral, except in those cases where the subject is unable to ingest, by herself, any medication. In those instances it may be necessary to administer the composition parenterally.

Depending on the intended mode, the compositions may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical excipient and an active compound of formula I or the pharmaceutically acceptable salts thereof and, in addition, may include other medicinal agents, pharmaceutical agents, carriers, adjuvants, diluents, etc.

The amount of active compound administered will, of course, be dependent on the subject being treated, the subject's weight, the manner of administration and the judgement of the prescribing physician. However, an effective dosage is in the range of about 1-2 mg/kg/day, preferably about 1 mg/kg/day. For an average 50 kg human, this would amount to about 50-100 mg/day, or preferably about 50 mg/day.

For solid compositions, conventional nontoxic solids include, for example, pharmaceutical grades of mannitol, lactose, starch, magnesium stearate, sodium saccharin, talc, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound(s), a fertility-controlling amount, i.e. in an amount effective to achieve the desired fertility control in the female subject being treated.

For oral administration, a pharmaceutically acceptable non-toxic composition is formed by the incorporation of any of the normally employed excipients described above. Such compositions take the form of solutions, suspensions, tablets, pills, capsules, powders, sustained release formulations and the like. Such compositions may contain 1%-95% active ingredient, preferably 1-70%.

Parenteral administration, if used, is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently revised approach for parenteral administration employs the implantation of a slow-release or sustained-release system, such that a constant level of dosage is maintained. See, e.g., U.S. Pat. No. 3,710,795, which is incorporated herein by reference.

The following examples serve to illustrate the invention. They should not be construed as narrowing it, or limiting its scope. The Steps A, B, C, etc. cited below refer to the corresponding Steps in Reaction Sequence 1.

EXAMPLE 1

Step A $17\beta$-Tetrahydropyranyloxy-$5\alpha$-estr-1-en-3-one (Compound 2)

A solution of 1.15 g of $17\beta$-hydroxy-$5\alpha$-estr-1-en-3-one, Compound 1, in 20 ml of dichloromethane is cooled to 0° C. in an ice bath. To this solution is added 0.5 ml of dihydropyran and 0.060 g of p-toluenesulfonic acid, and the reaction mixture is stirred at 0° C. for 2 hr. Since some starting material is still present, 0.2 ml of dihydropyran and 0.02 of p-toluenesulfonic acid is added, and the reaction mixture is stirred for an additional hour. Sodium bicarbonate (0.7 g) is added, and the reaction mixture is stirred for 0.5 hr. Diethylether (20 ml) is added, and the mixture is filtered through 8 g of Florisil ®. The Florisil is rinsed with dichloromethane and ether. Evaporation of the solvent produces 1.72 g of a yellowish oil, which is purified using 55 g of Florisil and eluted with 33% ethyl acetate in hexane to give 1.23 g of pure $17\beta$-tetrahydropyranyloxy-$5\alpha$-estr-1-ene-3-one.

EXAMPLE 2

Step B $17\beta$-Tetrahydropyranyloxy-3-diethylphosphato-$5\alpha$-estr-2-ene-3-one (Compound 3)

To a 100-ml, 3-necked flask equipped with a magnetic stirrer, dry-ice condenser, and an ammonia gas inlet tube under argon is condensed 55 ml of ammonia while the flask is cooled using a Dry Ice-acetone bath. Lithium wire (0.046 g cut into small pieces) is added and the mixture is stirred for 15 min. Next, 10 ml of tetrahydrofuran is added, followed by dropwise addition of 1.20 g of $17\beta$-tetrahydropyranyloxy-$5\alpha$-estr-1-en-3-one dissolved in 10 ml of dry tetrahydrofuran. The blue color remains during the addition, but fades shortly after. Lithium metal (0.005 g) is added, and the reaction mixture remains blue during 2 hr of stirring at −78° C. The Dry Ice-acetone bath is removed and the ammonia is evaporated under a stream of argon. Finally, the tetrahydrofuran is removed under vacuum. The tan, gummy residue is treated with dry tetrahydrofuran (8 ml) and dry N,N,N',N'-tetramethylethylenediamine, and most of the gum dissolves. The solution is treated with 1.2 ml of diethylchlorophosphate, and the reaction mixture becomes clear and warms up. Precipitation begins after a short time. The reaction mixture is stirred at room temperature for 16 hr. The solvent is then evaporated under vacuum, and to the residue are added 70 ml of water and 70 ml of ether. The ether phase is separated, and the water phase is extracted with ether (2×50 ml). The combined ether phase is washed with water, and sodium chloride solution and dried. Evaporation of the solvent produces 1.33 g of an oil (Compound 3) which is used in Step C without further purification. Proof of structure is confirmed by the subsequent reactions.

EXAMPLE 3

Step C

17β-Tetrahydropyranyloxy-5α-estr-2-ene (Compound 4)

In a 200-ml, 3-necked flask equipped with a magnetic stirrer, ammonia gas inlet, and Dry-Ice condenser, under argon is condensed 60 ml of ammonia, while the flask is being submerged in a Dry-Ice/acetone bath. To the ammonia is added lithium metal (1.0 g cut into small pieces), and the mixture is stirred for 15 min. To this solution is added dropwise a solution of the crude enol-phosphate (1.33 g) dissolved in a mixture of tetrahydrofuran (13 ml) and t-butanol (13 ml). The cooling bath is removed after the complete addition, and the ammonia solution is allowed to reflux for 2 hr. The excess lithium is then destroyed by dropwise addition of t-butanol/ethanol mixture. The ammonia is allowed to evaporate under a stream of argon, and the remainder of the solvent is evaporated under reduced pressure. The residue is treated with water (70 ml) and ether (70 ml). The ether is separated and the water phase is extracted again with ether (50 ml). The combined ether phase is washed twice with water, (30 ml) and sodium chloride solution (30 ml) and dried over sodium sulfate. Evaporation of the solvent under reduced pressure produces 0.84 g of a yellow oil, which is purified on a Florisil column (ether/benzene. 50/50, v/v), producing 0.26 g of 17β-tetrahydropyranyloxy-5α-estr-2-ene.

The structure of Compound 4 is confirmed by the following data:

Proton magnetic resonance spectrum (90 MHz in CDCl$_3$): δ: 5.66, 5.62 (d, 2H, 2C$\underline{H}$ and 3—C$\underline{H}$), 4.62 (s, 1H, 2' isometric proton), 3.3–4.05 (m, 1H, 17a—C$\underline{H}$ and 2H 6'—C$\underline{H_2}$; 0.80, 0.78 (d, 3H, 18—C$\underline{H_3}$).

EXAMPLE 4

Step D

17β-Hydroxy-5α-estr-2-ene (Compound 5)

To a solution of 0.25 g of 17β-tetrahydropyranyloxy-5α-estr-2-en, Compound 4, in 8 ml of methanol is added 1N hydrochloric acid (0.2 ml) and the reaction mixture is stirred at room temperature for 6 hr. Evaporation of the solvent under vacuum produces a residue of white crystals. The residue is treated with water (15 ml) and ether (25 ml). The ether phase is separated, and the water is extracted once more with 12 ml of ether. The combined ether phase is washed with water, sodium chloride solution, and dried over sodium sulfate. Evaporation of the solvent produces 0.19 g of 17β-hydroxy-5α-estr-2-ene. The structure of the Compound 5, is confirmed by the following spectral data:

Proton magnetic resonance spectrum (90 MHz in CDCl$_3$): δ: 5.67, 5.63 (d, 2H, 2—C$\underline{H}$ and 3—C$\underline{H}$), 1.56 (s, 1H, 17—O$\underline{H}$), 0.76 (s, 3H, 18—C$\underline{H_3}$).

Anal. Mass Spectrum for C$_{18}$H$_{28}$O: Calcd: 260; Found: 260.

EXAMPLE 5

Step E

5α-Estr-2-en-17-one (Compound 6)

To a solution of 0.18 g of 17β-hydroxy-5α-estr-2-ene, Compound 5, in 10 ml of acetone cooled to 0°–5° C. is added dropwise Jones reagent until the reaction mixture becomes permanently orange-brown. The reaction mixture is stirred for another 2 min, and then the excess reagent is destroyed by addition of isopropanol. The solvent is evaporated under reduced pressure, and the residue is treated with water (25 ml) and ether (25 ml). The ether phase is separated, and the water is extracted once more with ether (20 ml). The combined ether phase is washed with water, sodium chloride solution and dried over sodium sulfate. Evaporation of the solvent produces 0.175 g of 5α-estr-2-ene-17-one.

The structure of Compound 6 is confirmed by the following spectral data:

Proton magnetic resonance spectrum (90 MHz in CDCl$_3$): δ: 5.66, 5.63 (d, 2H, 2—C$\underline{H}$ and 3—C$\underline{H}$); 0.88 (s, 3H, 18—C$\underline{H_3}$).

Anal. Mass Spectrum for C$_{18}$H$_{26}$O: Calcd: 258; Found: 258.

EXAMPLE 6

Step F

17β-Hydroxy-17α-ethynyl-5α-estr-2-ene (Compound Ia)

To 20 ml of dry tetrahydrofuran at 0° C. is added 0.75 ml of ethylmagnesium bromide (3 molar in ethyl ether) and through this solution is passed a stream of acetylene gas. After 30 min, 0.50 of ethylmagnesium bromide was added, followed after 30 min by another 0.50 ml of ethylmagnesium bromide. Acetylene gas is passed through the mixture all the time, and is continued for another 2 hr after the last addition. To the Grignard reagent is added dropwise 0.160 g of 5α-estr-2-en-17-one, Compound 6, dissolved in 5 ml of dry tetrahydrofuran. The combined reaction mixture is stirred at 0° C. for 2 hr, and then at room temperature for 16 hr. To the reaction mixture is added dropwise saturated ammonium chloride solution, water (30 ml) and ether (30 ml). The organic phase is separated, and the water phase is extracted once more with 12 ml of ether. The combined organic phase is washed twice with sodium chloride solution and dried over sodium sulfate. Evaporation of the solvent gave a brownish oil, which was purified on a silica gel column to give 0.087 g of Compound Ia, mp 107.5°–109° C.

The structure of Compound Ia is confirmed by the following spectral data:

Proton magnetic resonance spectrum (90 MHz in CDCl$_3$): δ: 5.66, 5.63 (d, 2H, 2—C$\underline{H}$ and 3—C$\underline{H}$); 2.57 (s, 1H, 21—C≡C$\underline{H}$), 1.56 (s, 17—O$\underline{H}$); and 0.87 (s, 3H, 18—C$\underline{H_3}$).

Anal. Mass Spectrum for C$_{20}$H$_{28}$O: Calcd: 284; Found: 284.

EXAMPLE 7

Step G

17α-Ethynyl-17β-propionyloxy-estra-2-ene
(Compound Ib where R¹ is acyl and R² is ethyl)

(a) To a solution of 1.0 g of Compound Ia (e.g. from Step F) and 20 ml of dry pyridine (dried over potassium hydroxide pellets) is added 3 ml of propionic anhydride followed by stirring at ambient temperature for 42 hr. The mixture is added to 150 ml of a 3% hydrochloric acid solution, and the precipitate is extracted into three 80 ml portions of diethylether. The combined ether extracts are washed once with 100 ml of water, dried using anhydrous sodium sulfate, and evaporated to dryness using reduced pressure. A crystalline residue of 1.1 g of Compound Ib is obtained, which is recrystallized from ether-hexane to produce an analytical sample of the acylated product.

(b) Similarly, proceeding as in Subpart (a) above of this example, but substituting a stoichiometrically equivalent amount of
acetic anhydride;
butanoic anhydride;
isobutanoic anhydride;
n-octanoic anhydride;
dodecanoic anhydride;
hexadecanoic anhydride;
eicosanoic anhydride;
tetracosanoic anhydride;
acrylic anhydride;
methacrylic anhydride;
3-methylacrylic anhydride;
2-octenoyl anhydride;
2-hexadecenoyl anhydride;
2-tetracosenoyl anhydride;
propynoic anhydride;
2-hexynoic anhydride;
2-hexadecynoyl anhydride;
2-tetracosynoyl anhydride;
2-chloroacetic anhydride;
3-bromopropionoyl anhydride;
2-chlorohexanoyl anhydride;
2-chlorohexadecanoylanhydride;
2-chlorotetracosanoyl anhydride;
benzoyl anhydride;
4-chlorobenzoyl anhydride;
4-methylbenzoyl anhydride;
2-naphthoic anhydride;
4-chloro-2-naphthoyl anhydride;
6-bromo-2-naphthoyl anhydride;
phenylacetic anhydride;
3-phenylpropionic anhydride; or
6-phenylhexanoyl anhydride for propionic anhydride,
the following esters of Compound Ib are obtained:
17α-ethynyl-17β-acetyloxy-estra-2-ene;
17α-ethynyl-17β-butanoyloxy-estra-2-ene;
17α-ethynyl-17β-isobutanoyloxy-estra-2-ene;
17α-ethynyl-17β-n-octanoyloxy-estra-2-ene;
17α-ethynyl-17β-dodecanoyloxy-estra-2-ene;
17α-ethynyl-17β-hexadecanoyloxy-estra-2-ene;
17α-ethynyl-17β-eicosanoyloxy-estra-2-ene;
17α-ethynyl-17β-tetracosanoyloxy-estra-2-ene;
17α-ethynyl-17β-acryloyloxy-estra-2-ene;
17α-ethynyl-17β-methacryloyloxy-estra-2-ene;
17α-ethynyl-17β-(3-methylacryloyloxy)-estra-2-ene;
17α-ethynyl-17β-(2-octenoyloxy)-estra-2-ene;
17α'ethynyl-17β-(2-hexadecenoyloxy)-estra-2-ene;
17α-ethynyl-17β-(2-tetracosenoyloxy)-estra-2-ene;
17α-ethynyl-17β-propynyloxy-estra-2-ene;
17α-ethynyl-17β-(2-hexynyloxy)-estra-2-ene;
17α-ethynyl-17β-(2-hexadecynyloxy)-estra-2-ene;
17α-ethynyl-17β-(2-tetracosynyloxy)-estra-2-ene;
17α-ethynyl-17β-(2-chloroacetyloxy)-estra-2-ene;
17α-ethynyl-17β-(3-bromopropionyloxy)-estra-2-ene;
17α-ethynyl-17β-(2-chlorohexanoyloxy)-estra-2-ene;
17α-ethynyl-17β-(2-chlorohexadecanoyloxy)-estra-2-ene;
17α-ethynyl-17β-(2-chlorotetraeicosanoyloxy)-estra-2-ene;
17α-ethynyl-17β-benzoyloxy-estra-2-ene;
17α-ethynyl-17β-(4-chlorobenzoyloxy)-estra-2-ene;
17α-ethynyl-17β-(4-methylbenzoyloxy)-estra-2-ene;
17α-ethynyl-17β-(2-naphthoyloxy)-estra-2-ene;
17α-ethynyl-17β-(4-chloro-2-naphthoyloxy)-estra-2-ene;
17α-ethynyl-17β-(6-bromo-2-naphthoyloxy)-estra-2-ene;
17α-ethynyl-17β-phenylacetyloxy-estra-2-ene;
17α-ethynyl-17β-(3-phenylpropionoyloxy)-estra-2-ene; or
17α-ethynyl-17β-(6-phenylhexanoyloxy)-estra-2-ene.

(c) Similarily, proceeding as in Subpart (a) above of this Example but substituting a stoichiometrically equivalent amount of
acetyl chloride;
propionyl chloride;
n-octanoyl chloride;
eicosanoyl chloride;
acryloyl chloride;
methacryloyl chloride;
2-tetracosenoyl chloride;
propynoyl chloride;
2-tetracosynoyl chloride;
2-chloracetyl chloride;
2-chlorotetracosanoyl chloride;
benzoyl chloride;
4-chlorobenzoyl chloride;
4-methylbenzoyl chloride;
2-naphthoyl chloride;
6-bromo-2-naphthoyl chloride;
phenylacetyl chloride;
3-phenylpropionyl chloride; or
6-phenylhexanoyl chloride for propionyl anhydride,
the following esters of Compound 9 are obtained:
17α-ethynyl-17β-acetyloxy-estra-2-ene;
17α-ethynyl-17β-propionyloxy-estra-2-ene;
17α-ethynyl-17β-n-octanoyloxy-estra-2-ene;
17α-ethynyl-17β-eicosanoyloxy-estra-2-ene;
17α-ethynyl-17β-acryloyloxy-estra-2-ene;
17α-ethynyl-17β-methacryloyloxy-estra-2-ene;
17α-ethynyl-17β-2-tetracosenyloxy-estra-2-ene;
17α-ethynyl-17β-propynoyloxy-estra-2-ene;
17α-ethynyl-17β-2-tetracosynyloxy-estra-2-ene;
17α-ethynyl-17β-2-chloroacetyloxy-estra-2-ene;
17α-ethynyl-17β-2-chlorotetracosanoyloxy-estra-2-ene;
17α-ethynyl-17β-benzoyloxy-estra-2-ene;
17α-ethynyl-17β-4-chlorobenzoyloxy-estra-2-ene;
17α-ethynyl-17β-4-methylbenzoyl-estra-2-ene;
17α-ethynyl-17β-2-naphthoyloxy-estra-2-ene;
17α-ethynyl-17β-6-bromo-2-naphthoyloxy-estra-2-ene;
17α-ethynyl-17β-phenylacetyloxy-estra-2-ene;
17α-ethynyl-17-β-3-phenylpropionoyloxy-estra-2-ene; or
17α-ethynyl-17β-6-phenylhexanoyloxy-estra-2-ene.

The following illustrates the preparation of representative pharmaceutical formulations containing an active compound of formula I, e.g. 17α-ethynyl-17β-propionyloxy-estra-2-ene.

| I.V. Formulation | |
|---|---|
| Active compound | 2.5 g |
| Propylene glycol | 20.0 g |
| POLYETHYLENE GLYCOL 400 | 20.0 g |
| TWEEN 80 | 1.0 g |
| 0.9% Saline solution | 100.0 ml |

In Examples 8 through 15, the active ingredient is 17α-ethynyl-estra-2-en-17β-ol. Other compounds of formula I may be substituted therein.

| TABLETS | |
|---|---|
| Ingredients | Quantity per tablet, mgs. |
| Active ingredient | 100 |
| cornstarch | 20 |
| lactose, spray-dried | 153 |
| magnesium stearate | 2 |

The above ingredients are thoroughly mixed and pressed into single scored tablets.

| CAPSULES | |
|---|---|
| Ingredients | Quantity per capsule, mgs. |
| Active ingredient | 100 |
| lactose, spray-dried | 148 |
| magnesium stearate | 2 |

The above ingredients are mixed and introduced into a hard-shell gelatin capsule.

| TABLETS | |
|---|---|
| Ingredients | Quantity per tablet, mgs. |
| Active ingredient | 100 |
| cornstarch | 50 |
| lactose | 145 |
| magnesium stearate | 5 |

The above ingredients are mixed intimately and pressed into single scored tablets.

| CAPSULES | |
|---|---|
| Ingredients | Quantity per capsule, mgs. |
| Active ingredient | 100 |
| lactose | 15 |
| cornstarch | 25 |
| magnesium stearate | 2 |

The above ingredients are mixed and introduced into a hard-shell gelatin capsule.

| CAPSULES | |
|---|---|
| Ingredients | Quantity per capsule, mgs. |
| Active ingredient | 100 |
| lactose | 92 |

The above ingredients are mixed and introduced into a hard-shell gelatin capsule.

INJECTABLE PREPARATION

An injectable preparation buffered to a pH of 7 is prepared having the following composition:

| Ingredients | |
|---|---|
| Active ingredient | 100 mg |
| $KH_2PO_4$ buffer (0.4M solution) | 2 ml |
| KOH (1N) | q.s. to pH 7 |
| water (distilled, sterile) | q.s. to 20 ml |

ORAL SUSPENSION

An oral suspension is prepared having the following composition:

| Ingredients | |
|---|---|
| Active ingredient | 2 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

While the present invention has been described with reference to the specific embodiments thereof, it should be understood by those skilled in this art that various changes may be made and equivalents may be substituted without departing from the true spirit and scope of the invention.

What is claimed is:

1. Stereoisomerically pure 17α-ethynyl-estra-2-en-17β-ol consisting of not less than 99% of the Δ2 isomer and not more than 1% of other materials.

2. A stereoisomerically pure 17β-ester of 17α-ethynyl-estra-2-en-17β-ol of the formula:

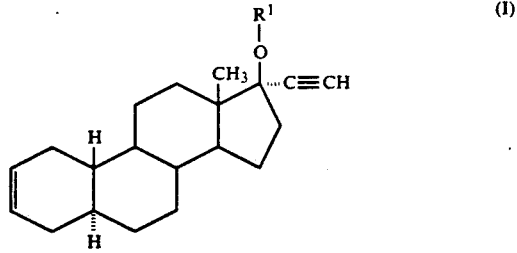

wherein: $R^1$ is an acyl group of the formula:

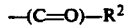

—(C=O)—$R^2$ wherein:
$R^2$ is an organic substituent selected from the group consisting of alkyl, alkenyl, alkynyl, cycloalkyl, cycloalkylalkylene, haloalkyl, aryl, haloaryl and arylalkylene consisting of not less than 99% of the Δ2 isomer and not more than 1% of other materials.

3. The ester of claim 2 wherein $R^2$ is alkyl.
4. The ester of claim 3 wherein $R^2$ is ethyl.
5. The ester of claim 2 wherein $R^2$ is aryl.

6. The ester of claim 2 wherein R² is arylalkylene.
7. A 3-phosphato-5α-estr-2-ene of the formula:

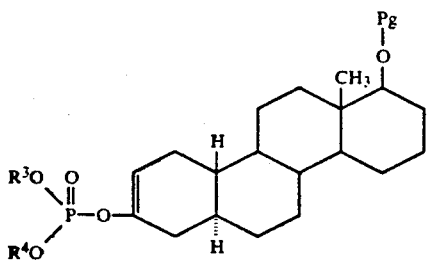

wherein:
R³ and R⁴ are independently selected from lower alkyl containing 1 to 6 carbon atoms; and
Pg is an oxygen protecting group selected from the group consisting of tetrahydropyran, t-butyldimethylsilyl and β-methoxy ethyl ether.

8. The 3-phosphato-5α-estr-2-ene of claim 7 wherein Pg is tetrahydropyranyl.
9. The 3-phosphato-5α-estr-2-ene of claim 8 wherein R³ and R⁴ are each ethyl.
10. A process for stereospecifically introducing Δ²-unsaturation into a 19-nor steroid structure which process comprises converting a 3-keto steroid to the corresponding 3-substituted phosphate with dialkylchlorophosphate and reducing said 3-substituted phosphate with a strong reducing agent.
11. The process of claim 10 wherein said strong reducing agent is lithium and ammonia.
12. A process for the preparation of a compound of the formula:

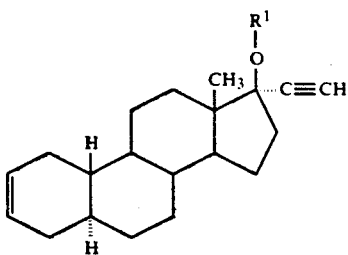

wherein: R¹ is hydrogen, which process comprises:
(a) reacting the 17β-hydroxy group of 17β-hydroxy-5α-estr-1-en-3-one with dihydropyran to produce the 3-keto-17β-ether;
(b) reducing the 3-keto-17β-ether product of step (a) with lithium in ammonia;
(c) reacting the product of step (b) with dialkyl chlorophosphate to produce the 3-substituted phosphate;
(d) reducing the product of step (c) with lithium and ammonia to produce the Δ²-protected-17β-ether product;
(e) hydrolysis of the produce of step (d) to produce the Δ²-17β-hydroxy compound;
(f) oxidizing the 17β-hydroxy product of step (e) to produce the 17-keto compound; and
(g) reacting the 17-keto derivative of step (f) with acetylene magnesium halide to produce the compound of formula I wherein R¹ is hydrogen.

13. A process for the preparation of a compound of the formula:

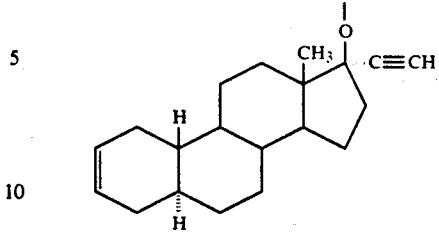

wherein R¹ is an acyl substituent of the formula:

—(C=O)—R² wherein: R² is an organic substituent selected from the group consisting of alkyl, alkenyl, alkynyl, cycloalkyl, cycloalkylalkylene, haloalkyl, aryl, haloaryl and arylalkylene, which process comprises the process of claim 12 followed by the additional step of:
(h) reacting the product of step (g) with an acyl halide or any acyl anhydride to produce the compound of formula I wherein R¹ is an acyl substituent of the formula —(C=O)R².

14. The process of claim 13 wherein R² is an alkyl, an aryl or an arylalkylene.
15. The process of claim 14 wherein R² is ethyl.
16. A pharmaceutical composition useful in achieving fertility control in a female mammal which composition comprises a fertility controlling effective amount of a stereoisomerically pure steroid consisting of not less than 99% of the Δ² compound of the formula:

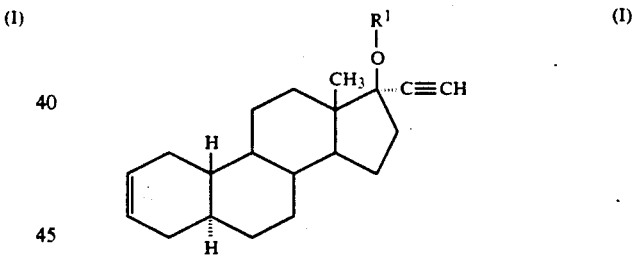

wherein: R¹ is hydrogen or

—(C=O)—R² wherein: R² is an organic substituent selected from the group consisting of alkyl, alkenyl, alkynyl, cycloalkyl, cycloalkylalkylene, haloalkyl, aryl, haloaryl and arylalkylene and less than 1% of other materials in admixture with a pharmaceutically acceptable excipient.

17. The composition of claim 15 wherein in the compound of formula I, R¹ is hydrogen.
18. The composition of claim 15 wherein in the compound of formula I, R¹ is acyl.
19. The composition of claim 18 wherein said acyl is —(C=O)—R², where R² is alkyl.
20. The composition of claim 19 wherein said alkyl group is ethyl.
21. A method of contraception in female mammals which method comprises administrating to such mammal an antiprogestational fertility controlling effective amount of the compound of formula:

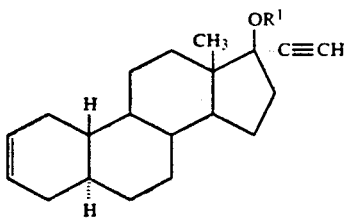

wherein $R^1$ is hydrogen or

—(C=O)—$R^2$ wherein $R^2$ is an organic substituent selected from the group consisting of alkyl, alkenyl, alkynyl, cycloalkyl, cycloalkylalkylene, haloalkyl, aryl, haloaryl and arylalkylene, wherein said compound contains not less than 99% of the $\Delta^2$ isomer and not more than 1% of other materials.

22. The method of claim 21 wherein in said method said compound is orally administered.

23. The method of claim 22 wherein in said method said mammal is a female human being.

24. The method of claim 23 wherein in the compound of formula I, $R^1$ is hydrogen.

25. The method of claim 23 wherein $R^1$ is —(C=O)—$C_2H_5$.

* * * * *